United States Patent [19]
Descent

[11] Patent Number: 5,710,404
[45] Date of Patent: Jan. 20, 1998

[54] PORTABLE HAND-HELD DEVICE FOR INCINERATING NEEDLES

[75] Inventor: Serge Jacques Descent, St. Petersburg, Fla.

[73] Assignee: Biotronix 2000, Inc., Canada

[21] Appl. No.: 688,817

[22] Filed: Jul. 26, 1996

[51] Int. Cl.⁶ .................. B23K 11/22; A61G 12/00; A61L 11/00
[52] U.S. Cl. .................................................. 219/68
[58] Field of Search .............................................. 219/68

[56] References Cited

U.S. PATENT DOCUMENTS

| | | |
|---|---|---|
| 3,796,359 | 3/1974 | Dick . |
| 4,628,169 | 12/1986 | Ching-Lung ............... 219/68 |
| 4,877,934 | 10/1989 | Spinello ...................... 219/68 |
| 4,965,426 | 10/1990 | Colombo ..................... 219/68 |
| 5,076,178 | 12/1991 | Kohl et al. ................. 219/68 |
| 5,091,621 | 2/1992 | Butler ........................ 219/68 |
| 5,138,124 | 8/1992 | Kirk et al. ................. 219/68 |
| 5,212,362 | 5/1993 | Burden et al. ............. 219/68 |
| 5,245,935 | 9/1993 | Fukuda ...................... 219/68 |
| 5,264,675 | 11/1993 | Butler ........................ 219/68 |
| 5,268,549 | 12/1993 | Butler ........................ 219/68 |
| 5,282,428 | 2/1994 | Greville et al. ........... 219/68 |
| 5,288,964 | 2/1994 | Walker et al. ............. 219/68 |
| 5,294,767 | 3/1994 | Cantarero ................... 219/68 |
| 5,300,752 | 4/1994 | Elmerick et al. .......... 219/68 |
| 5,329,087 | 7/1994 | Kohl et al. ................. 219/68 |
| 5,334,812 | 8/1994 | Hsieh .......................... 219/68 |
| 5,336,862 | 8/1994 | Yelvington ................. 219/68 |
| 5,391,849 | 2/1995 | Furuya et al. ............. 219/68 |
| 5,468,928 | 11/1995 | Yelvington ................. 219/68 |
| 5,525,772 | 6/1996 | Tanguy ....................... 219/68 |
| 5,540,416 | 7/1996 | Huang ......................... 219/68 |
| 5,545,869 | 8/1996 | Piva ............................ 219/68 |
| 5,548,095 | 8/1996 | Cornell ....................... 219/68 |
| 5,551,355 | 9/1996 | Haines et al. ............. 219/68 |
| 5,637,238 | 6/1997 | Truesdale et al. ........ 219/68 |

FOREIGN PATENT DOCUMENTS

| | | |
|---|---|---|
| 2038884 | 3/1991 | Canada . |
| 2048827 | 8/1991 | Canada . |
| 2070211 | 6/1992 | Canada . |
| 2139347 | 6/1993 | Canada . |
| 2164133 | 6/1994 | Canada . |

Primary Examiner—Geoffrey S. Evans
Attorney, Agent, or Firm—James E. Larson; Larson & Larson, P.A.

[57] ABSTRACT

A portable hand-held device facilitates incineration of needles such as those used in hypodermic syringes. Incineration of such needles precludes the spread of diseases and the possibility of contamination of personnel handling such needles. The device includes two electrodes that are interconnected to complete the circuit when a needle is inserted into a recess in the device. A groove in the guide for the hand-held device allows full insertion of the a syringe to facilitate complete incineration of the needle, leaving little or no residue behind. An ambient temperature sensor senses the temperature adjacent the electrodes and cuts off power when the temperature exceeds a pre-set level.

13 Claims, 5 Drawing Sheets

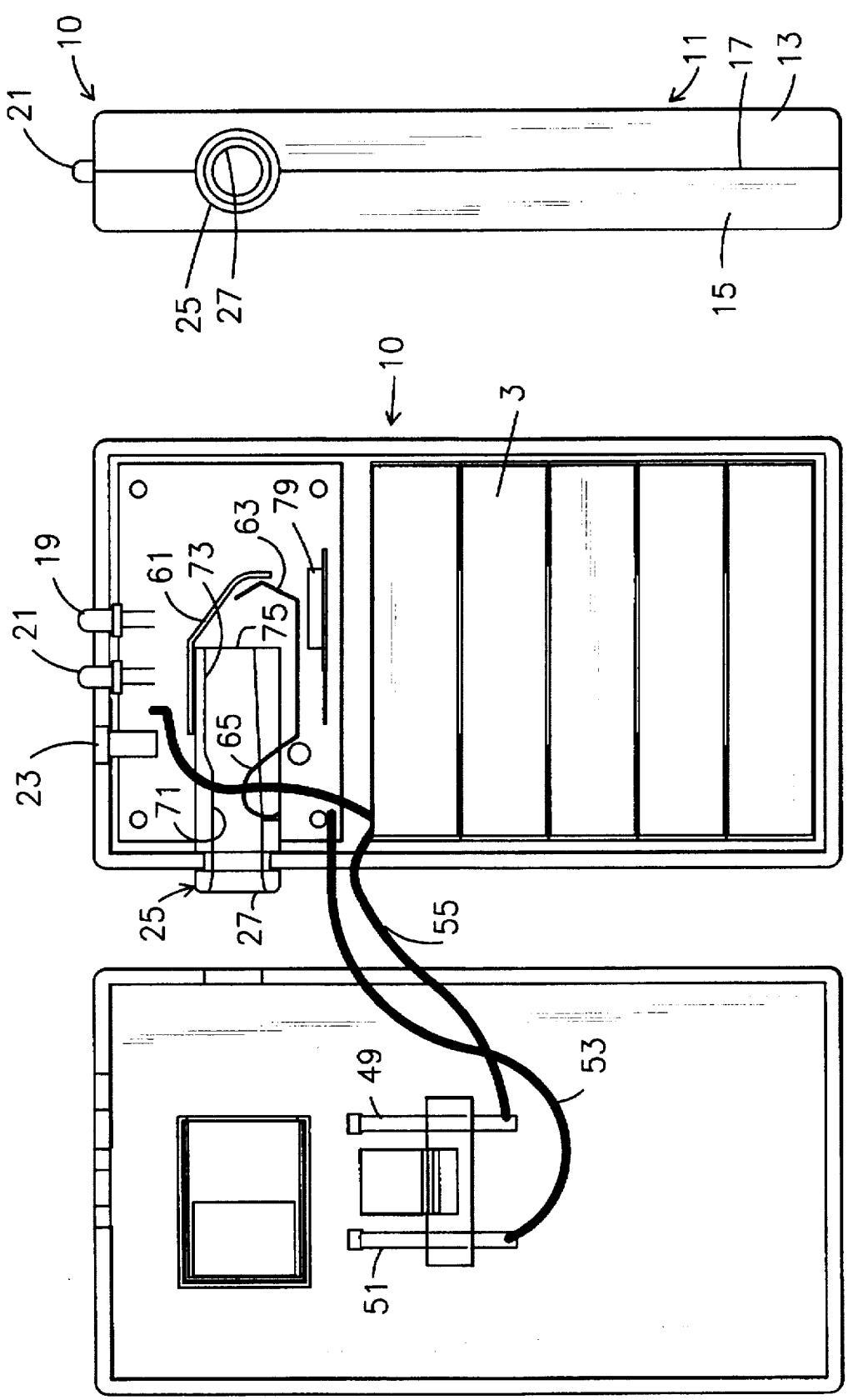

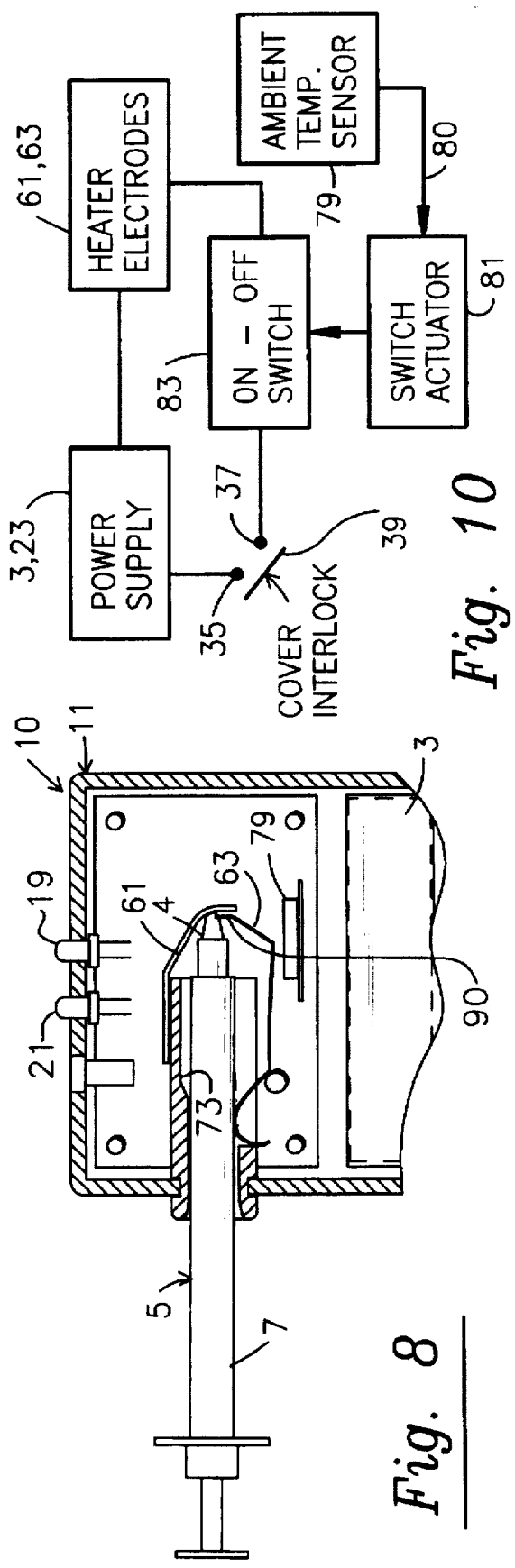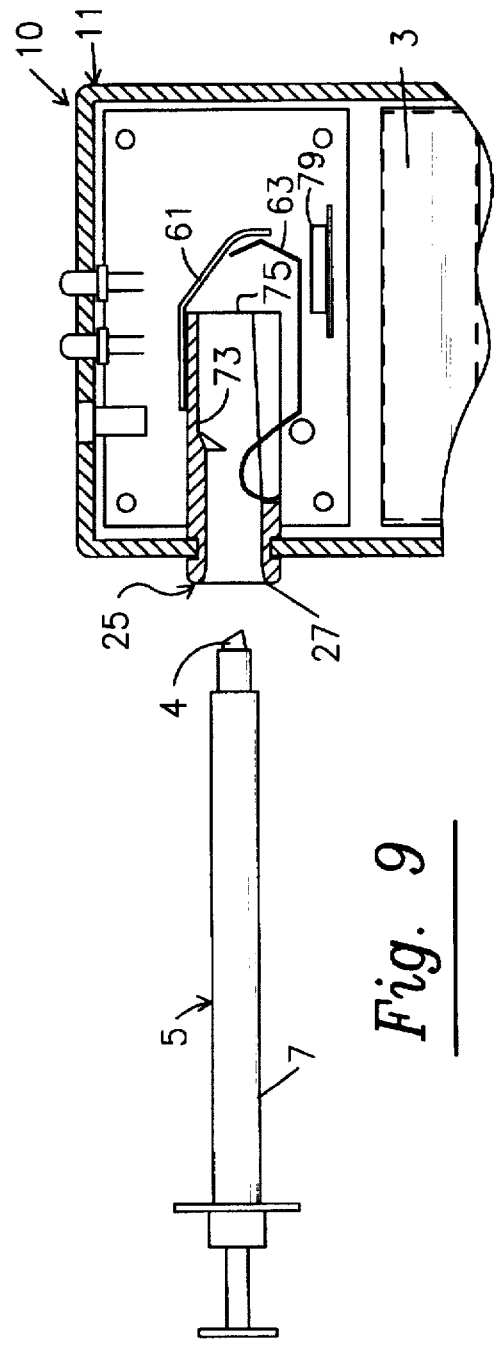

PORTABLE HAND-HELD DEVICE FOR INCINERATING NEEDLES

BACKGROUND OF THE INVENTION

The present invention relates to a portable hand-held device for incinerating needles. In the prior art, such devices are known. Applicant is aware of the following United States Patents:

U.S. Pat. No. 4,628,169 to Chíng-Lung
U.S. Pat. No. 4,877,934 to Spinello
U.S. Pat. No. 5,076,178 to Kohl et al.
U.S. Pat. No. 5,091,621 to Butler
U.S. Pat. No. 5,212,362 to Burden et al.
U.S. Pat. No. 5,245,935 to Fukuda
U.S. Pat. No. 5,264,675 to Butler
U.S. Pat. No. 5,282,428 to Greville et al.
U.S. Pat. No. 5,288,964 to Walker et al.
U.S. Pat. No. 5,294,767 to Cantarero
U.S. Pat. No. 5,300,752 to Elmerick et al.
U.S. Pat. No. 5,329,087 to Kohl et al.
U.S. Pat. No. 5,334,812 to Hsieh
U.S. Pat. No. 5,336,862 to Yelvington
U.S. Pat. No. 5,391,849 to Furuya et al.

While the above-listed United States Patents demonstrate that devices for incinerating needles are generally known, none of these references teaches all of the features and aspects of the present invention. A need has developed for a needle incinerating device that is extremely portable so that it may be carried conveniently by a person who is a diabetes patient and needs to carry insulin injectable devices wherever he or she travels. A need has also developed for such a device including safety features to prevent shock and injury to the operator as well as to preclude initiation of smoke and/or fire. It is with these needs in mind that the present invention was developed.

SUMMARY OF THE INVENTION

The present invention relates to a portable hand-held device for incinerating needles. The present invention includes the following interrelated objects, aspects and features:

(1) In a first aspect, the present invention is designed to be of extremely small size, of a size on the order of that of a television remote control device so that it may easily be held in the user's hand. The present invention is intended to be lightweight and self-contained with internal batteries employed as a power source. However, if desired, a receptacle may be provided on the device to allow electrical connection to an external source of either power or a battery recharger.

(2) The inventive device includes two electrodes that are in a circuit that is completed when a needle is inserted into the device and electrically interconnects the electrodes. A guideway is provided for the needle holder to linearly guide the needle holder as it is inserted further and further into the guideway while the entirety of the needle is being incinerated.

(3) Indicator lights are provided to allow external monitoring of the operation of the inventive system. An access door is provided to allow access to the chamber where incineration is conducted so that any debris created by the incineration process may be easily removed. The door includes safety features including an interlock disconnecting power from the electrodes when the door is removed and including a heat resistant pad to preclude melting of the housing during incineration.

(4) Adjacent the electrodes, an ambient temperature sensor is provided that senses the temperature of the atmosphere adjacent the electrodes. When this temperature exceeds a pre-set level, a switch actuator is activated to open the circuit and remove power from the electrodes.

Accordingly, it is a first object of the present invention to provide a portable hand-held device for incinerating needles.

It is a further object of the present invention to provide such a device including an access cover with an interlock preventing shock when the cover is removed.

It is a still further object of the present invention to provide such a device operable through the use of internal batteries and/or by employing an external power source.

It is a yet further object of the present invention to provide such a device including an ambient temperature sensor that senses temperature adjacent the electrodes thereof and disconnects power when the temperature exceeds a pre-set threshold.

These and other objects, aspects and features of the present invention will be better understood from the following detailed description of the preferred embodiment when read in conjunction with the appended drawing figures.

BRIEF DESCRIPTION OF TEE DRAWINGS

FIG. 2 shows a front view of the present invention with one half of the housing removed and pivoted 180° to show internal details.

FIG. 3 shows a side view of the present invention showing the guideway.

FIG. 8 shows a view similar to that of FIGS. 6 and 7 but with the hypodermic syringe completely inserted into the guideway and with the needle completely incinerated.

FIG. 9 shows a view similar to FIGS. 6–8 but showing the needle completely incinerated and the hub formerly surrounding the proximal end of the needle slightly melted.

FIG. 10 shows a schematic representation of some of the electrical circuitry of the present invention.

SPECIFIC DESCRIPTION OF THE PREFERRED EMBODIMENT

Figure 1:
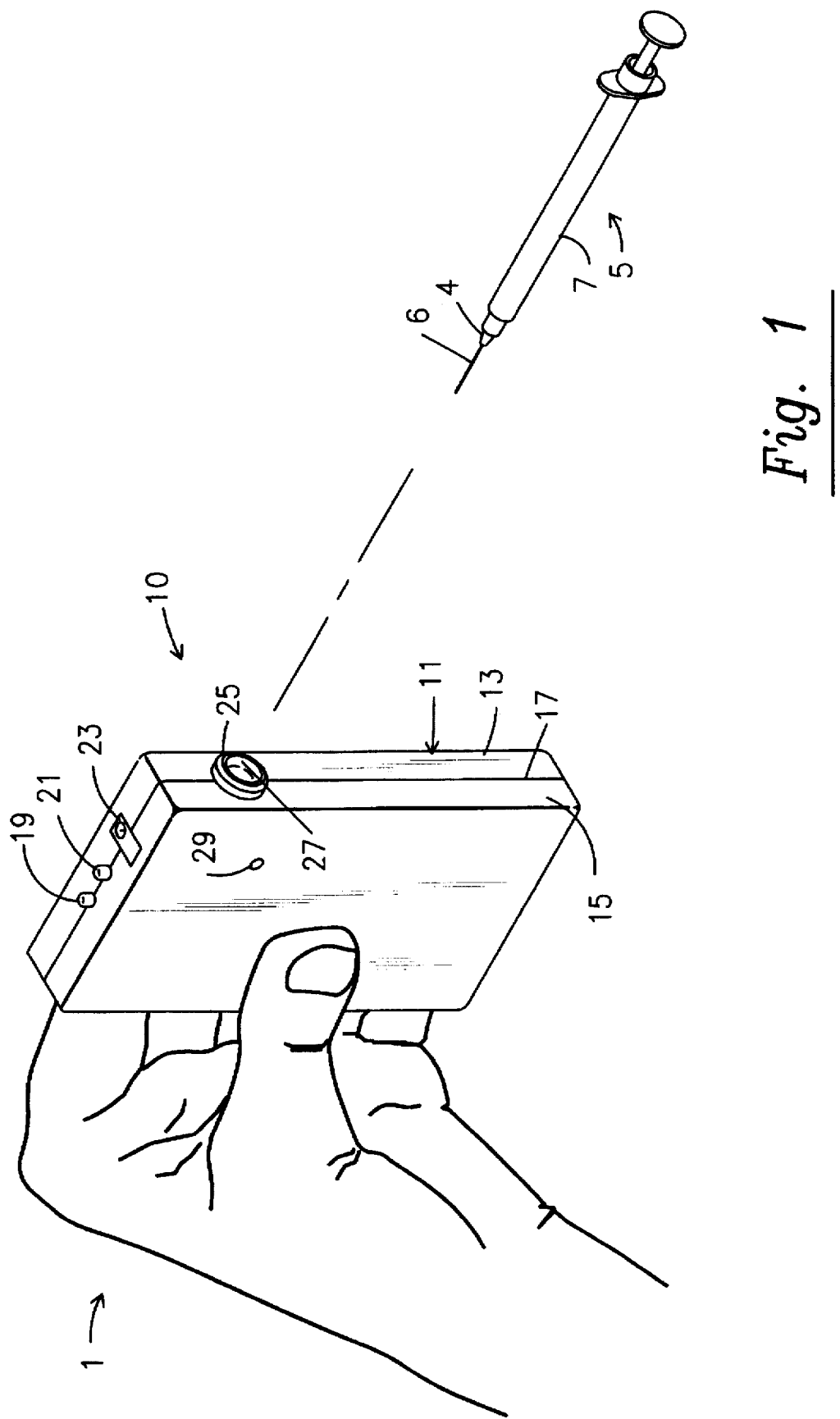
FIG. 1 shows a perspective view of the present invention.

With reference, first, to FIG. 1, the inventive device is generally designated by the reference numeral 10 and its small size is seen in comparison to the human hand 1 that is seen in FIG. 1 grasping the device. The small size and portability of the present invention are essential aspects thereof.

FIG. 1 also shows the device 10 to include a housing 11 having housing halves 13 and 15 interconnected at a seam 17 in a manner well known to those skilled in the art. Indicator lamps 19 and 21 may comprise green and red light emitting diodes, respectively, and are provided as indicators of the operation of the inventive device as will be described in greater detail hereinafter. FIG. 1 also shows an electrical receptacle 23. While, as seen in FIG. 2, the inventive device 10 may be powered using internal batteries 3, the receptacle 23 may, if desired, be electrically connected to a source of power to operate the device 10 or, alternatively, to a source of power to recharge the batteries 3.

A guideway 25 is also shown that includes an opening 27 for a purpose to be described in greater detail hereinafter. An additional indicator lamp 29 is also shown.

Figure 5:
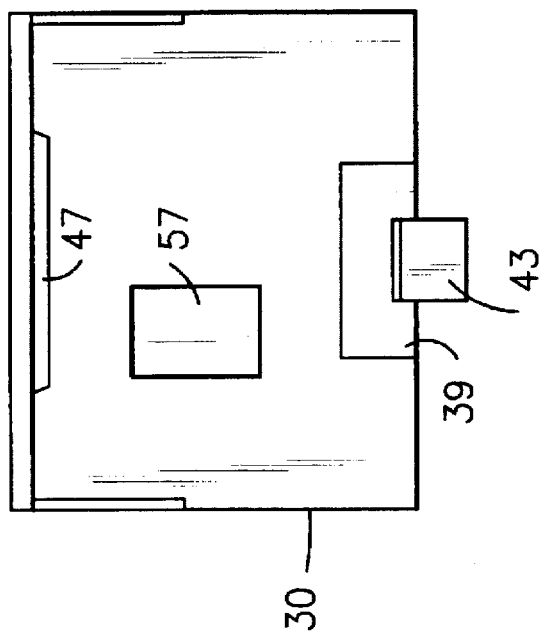
FIG. 5 shows a rear view of the access door that is removed from FIG. 4.
Figure 4:
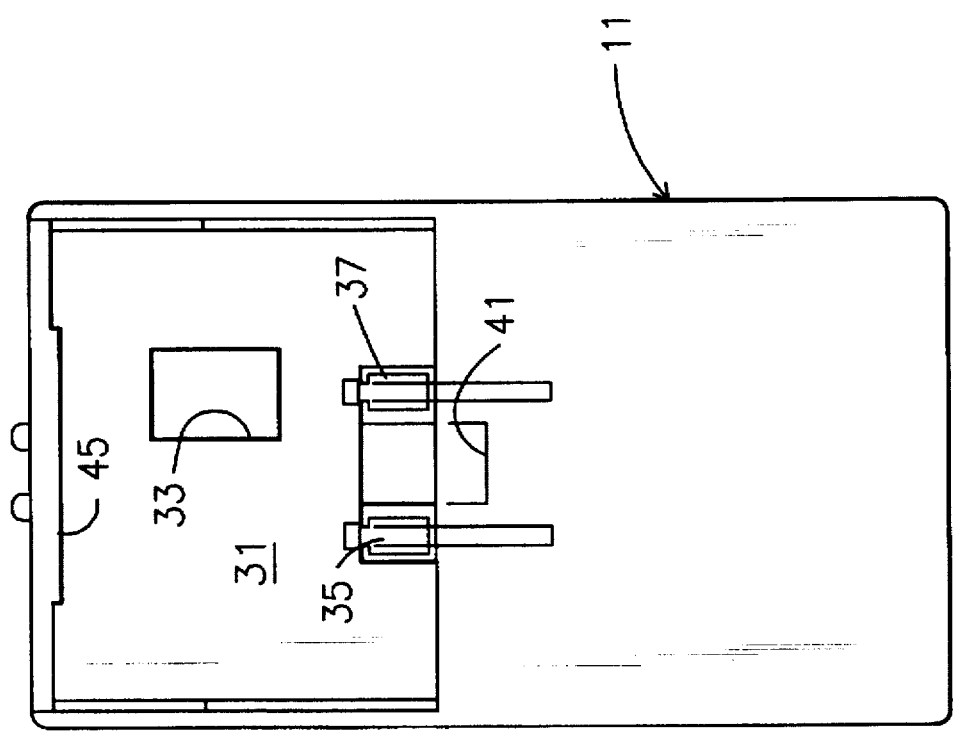
FIG. 4 shows a front view of the present invention with the access door removed.

With reference, now, to FIGS. 4 and 5, it is seen that the housing 11 includes an access cover 30 that, when removed, reveals an opening 31 leading to a side part 33 which in turn leads to a chamber within which needle incinerating electrodes are contained as will be described in greater detail hereinafter. At the lower portion of the opening 31, contacts 35 and 37 are provided. As seen in FIG. 5, an electrically conductive plate 39, such as a copper plate, is provided on the face of the cover 30 that faces the opening 31. FIG. 4 shows a recess 41 in the housing 11 that is designed to receive a locking tab 43 of the cover 30. A further recess 45 within the opening 31 of the housing 11 receives a downwardly depending tab 47 on the cover 30 so that the tab 47 may be inserted into the recess 45 and thereafter the cover may be pivoted to engage the tab 43 within the recess 41 to releasably lock the cover 30 on the housing 11. When the cover 30 is so locked on the housing 11, the plate 39 interconnects between the contacts 35 and 37 to complete a circuit therebetween. As seen in FIG. 2, the contacts 35 and 37 are interconnected with conductive pins 49, 51, respectively, which, via electrical conductors 53 and 55 complete the circuit when the cover 30 is placed in the assembled position on the housing 11. With reference to FIG. 10, the contacts 35 and 37 and the plate 39 are shown.

With reference back to FIGS. 4 and 5, the cover 30 has affixed thereon a heat resistant pad 57 that overlies the side part 33 in the housing 11 when the cover 30 is attached thereto. The heat resistant pad 57 protects the cover 30 and the housing 11 from heat generated within the side part 33 by operation of the needle incinerating electrodes.

Figure 6:
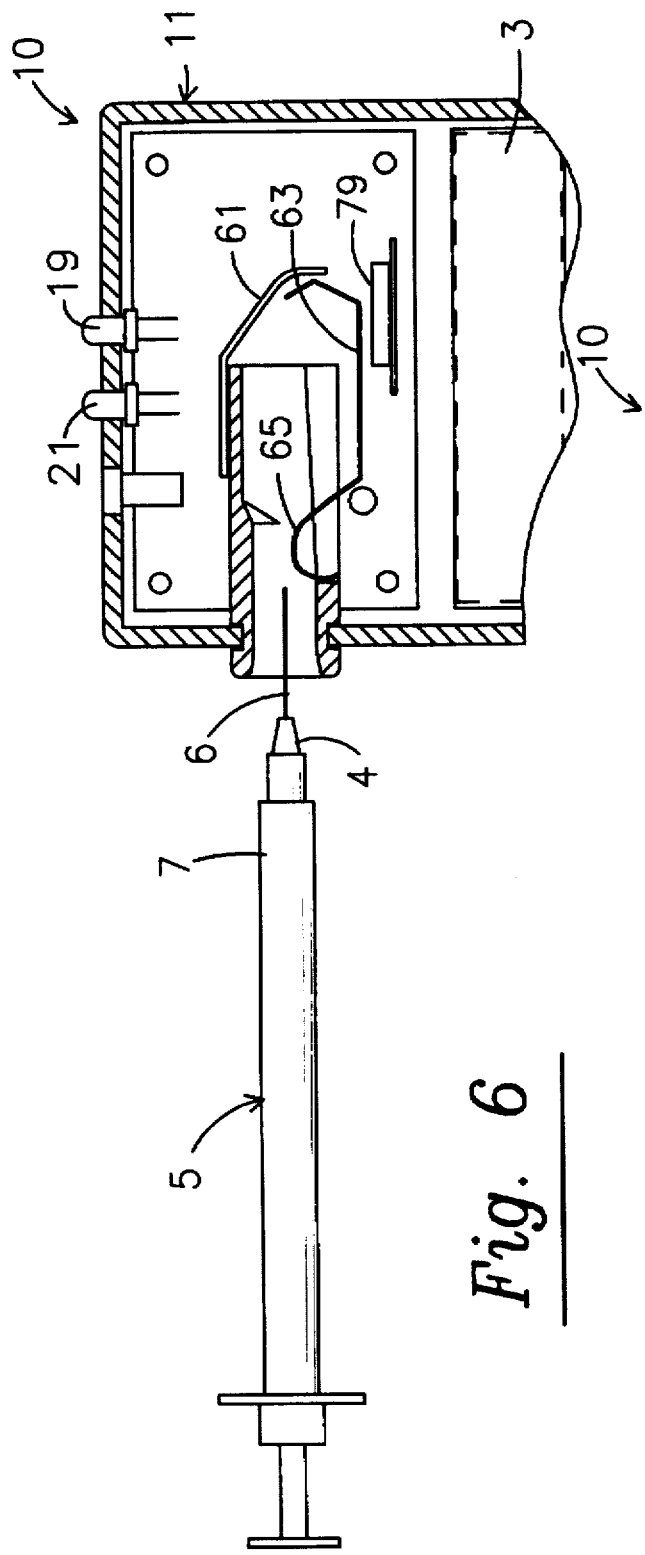
FIG. 6 shows a partial cross-sectional view with a hypodermic syringe partially inserted in the guideway.
Figure 7:
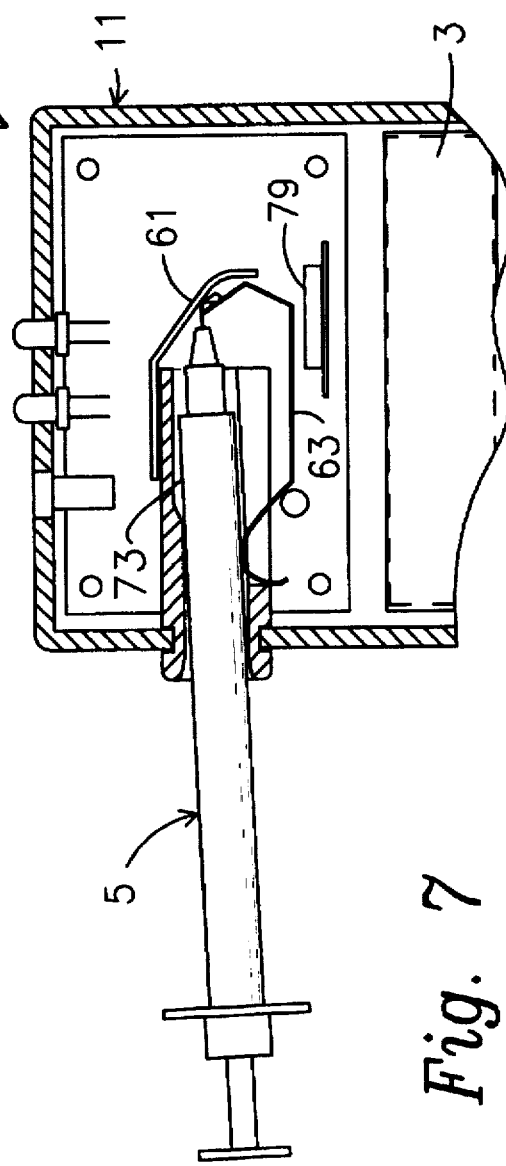
FIG. 7 shows a view similar to that of FIG. 6 but with the hypodermic syringe inserted further into the guideway and with the needle thereof further in the process of incineration.

The indicator lamps 19 and 21 seen in FIGS. 1, 2 and 6, in particular, are intended to facilitate monitoring of the operation of the system. The LED 19, preferably of a green color, is lit when power is applied to the system before incineration of a needle takes place. When incineration of a needle has successfully taken place, the LED 21, preferably of a red color, illuminates to indicate that the hypodermic syringe housing may be removed from the device 10. The indicator light 29 may be provided for any suitable purpose such as, for example, indicating current recharging of the batteries 3, or any other desired indication.

With further reference to FIG. 2, it is seen that the electrodes of the inventive device 10 consist of a rigid plate electrode 61 and a more resilient spring-like electrode 63 that includes a proximal portion 65 protruding within the guideway 25. The guideway 25 includes the opening or mouth 27 having a tapered opening as seen in FIGS. 2 and 6–9, an internal passageway 71, a groove 73, and a distal opening 75. The groove 73, as best seen from comparison of FIGS. 7 and 8, permits insertion of the body 7 of the syringe 5 completely within the guideway 25 to allow complete incineration of the entirety of the needle 6. The spring electrode 63 pushes the body 7 at the end of the insertion so that the hub 4 ends up touching end 90 of spring electrode 63 and end 90 is moved downward. This insures complete burn of the needle. As seen in FIGS. 1, 6 and 8, the hypodermic syringe 5 has a distal hub 4 surrounding the proximal end of the needle 6. With reference to FIG. 9, when incineration of the needle 6 is complete, and the remainder of the hypodermic syringe 5 is removed from the guideway 25, a portion of the hub 4 has been melted which ensures that the entirety of the syringe needle 6 has been incinerated.

With reference to FIGS. 6–9, it is seen that within the housing 11, an ambient temperature sensor 79 is provided adjacent the electrodes 61 and 63. The ambient temperature sensor 79 is provided to sense the temperature of ambient air adjacent the electrodes 61 and 63 and, when a pre-set temperature is exceeded, the ambient temperature sensor 79 is operative to open the circuit and remove electric power from the electrodes 61 and 63. This safety feature is provided to ensure that smoke and fire emanating from the device 10 are substantially precluded.

With reference to FIG. 10, a schematic representation of some of the electrical circuitry of the present invention is shown. The reference numerals 3, 23 are employed to refer to the power supply since the reference numeral 3 refers to the batteries internal to the housing 11 while the reference numeral 23 refers to the receptacle on the housing 11 that allows interconnection with a source of power. As explained hereinabove, the heater electrodes 61, 63 are spaced as shown in the drawings and electrical interconnection is made therebetween by the needle 6 of the syringe 5 as it is placed within the guideway 25.

The ambient temperature sensor 79 is shown adjacent the electrodes 61, 63 and is schematically shown to provide signals via the conductor 80 to a switch actuator 81 that controls operation of the on-off switch 83. Again, when the ambient temperature sensor 79 senses ambient temperature adjacent the electrodes 61, 63 that exceeds the pre-set threshold, such signals received by the switch actuator 81 cause the on-off switch 83 to turn to the off position opening the circuit and deactivating the electrodes 61, 63.

In the preferred embodiment of the present invention, the batteries 3 are five in number each of which is a 1.2 volt battery. In the preferred embodiment, the switch actuator 81 is pre-set to open the on-off switch 83 when the ambient temperature within the housing 11 exceeds 92° C. Applicant has found that 600 mega amps of current are required to incinerate a needle up to 40 gauge in size.

As such, an invention has been disclosed in terms of a preferred embodiment thereof which fulfills each and every one of the objects of the invention as set forth hereinabove and provides a new and useful portable hand-held device for incinerating needles of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A portable hand-held device for incinerating needles comprising:
   a) a compact housing sized to be hand-held;
   b) a chamber within said housing containing two adjacent electrodes one fixed in position and the other flexible, such electrodes connected into an electric circuit therewithin;
   c) a generally cylindrical guideway leading from said chamber to an opening accessible external to said housing, the guideway receiving a portion of the flexible electrode;
   d) a power supply connectable to said electrodes; and
   e) an ambient temperature sensor within said chamber, said sensor sensing temperature in said chamber and, responsive to sensing of temperature above a pre-set threshold, said sensor causing opening of a switch in said circuit to disconnect said power supply from said electrodes.

2. The device of claim 1, further wherein the fixed in position electrode is relatively rigid and the flexible electrode moves in response to pressure from a body of a syringe inserted into the guideway.

3. The device of claim 1, wherein said guideway has a tapered enlarged area adjacent said opening.

4. The device of claim 3, wherein said guideway has an internal groove adjacent said chamber permitting deep insertion of a syringe body into said chamber.

5. The device of claim 1, said housing further including a cover which, when removed, permits lateral access to said chamber via a side port.

6. The device of claim 5, wherein said cover includes an electrically conductive plate that engages two spaced contacts of said circuit when said cover is mounted on said housing, whereby when said cover is removed, said contacts are disconnected opening said circuit.

7. The device of claim 5, wherein said cover includes a heat resistant pad overlying said side port when said cover is mounted on said housing to isolate said cover and housing from heat in said chamber.

8. The device of claim 1, wherein said power supply comprises a battery within said housing.

9. The device of claim 1, wherein said power supply includes a receptacle on said housing connectable to an external power supply.

10. The device of claim 2, wherein the flexible electrode extends from the guideway to a position spaced apart from an end tip of the fixed electrode.

11. A portable hand-held device for incinerating a needle comprising:

(a) a compact housing sized to be hand-held;

(b) a chamber within said housing containing two adjacent electrodes, one fixed in position and the other flexible, such electrodes connected into an electric circuit therewithin;

(c) a generally cylindrical guideway leading from the chamber to an opening accessible external to said housing for receiving a needle, a needle hub and a syringe body, the guideway receiving through a side opening a first end of the flexible electrode with a second end outside the guideway spaced apart from an end of the fixed electrode, the second end of the flexible electrode moving in response to engagement with the needle hub to complete a burn of the entire needle; and (d) a power supply connectable to said electrodes.

12. The device according to claim 11 wherein the power supply is provided by five 1.2 volt batteries.

13. The device according to claim 11 wherein a switch within the compact housing turns off the power supply when the temperature within the housing exceeds 92 degrees Centigrade.

* * * * *